(12) United States Patent
Strothmann et al.

(10) Patent No.: US 10,463,666 B2
(45) Date of Patent: Nov. 5, 2019

(54) PHARMACEUTICAL COMPOSITION COMPRISING PROGESTOGENS AND/OR ESTROGENS AND 5-METHYL-(6S)-TETRAHYDROFOLATE

(71) Applicants: MERCK & CIE, Schaffhausen (CH); Bayer Intellectual Property GmbH, Monheim (DE)

(72) Inventors: Kai Strothmann, Oberursel (DE); Gavin Welch Wasserfall-Smith, Berlin (DE); Klaus Pietrzik, Meckenheim (DE); Kristina King, Berlin (DE); Rudolf Moser, Schaffhausen (CH)

(73) Assignees: MERCK & CIE, Schaffhausen (CH); Bayer Intellectual Property GmbH, Monheim (DE)

( * ) Notice: Subject to any disclaimer, the term of this patent is extended or adjusted under 35 U.S.C. 154(b) by 201 days.

(21) Appl. No.: 14/965,173

(22) Filed: Dec. 10, 2015

(65) Prior Publication Data

US 2016/0095860 A1 Apr. 7, 2016

Related U.S. Application Data (63) Continuation of application No. 11/938,688, filed on Nov. 12, 2007, which is a continuation-in-part of application No. PCT/EP2006/004858, filed on May 15, 2006.

(30) Foreign Application Priority Data

May 13, 2005 (DE) .................. 10 2005 023 301
Apr. 3, 2006 (DE) .................. 10 2006 016 285

(51) Int. Cl.
*A61K 31/519* (2006.01)
*A61K 31/4415* (2006.01)
(Continued)

(52) U.S. Cl.
CPC ........ *A61K 31/519* (2013.01); *A61K 31/4415* (2013.01); *A61K 31/525* (2013.01);
(Continued)

(58) Field of Classification Search
None
See application file for complete search history.

(56) References Cited

U.S. PATENT DOCUMENTS 6,011,040 A 1/2000 Muller et al.
6,083,528 A 7/2000 Elliesen et al.
(Continued)

FOREIGN PATENT DOCUMENTS

DE 10022510 A1 11/2001
EP 0898965 A2 3/1999
(Continued)

OTHER PUBLICATIONS

"Structure-Activity Relationshi and Drug Design." Remington's Pharmaceutical Sciences (Sixteenth Edition). Mack Publishing. 1980. pp. 420-425.*
(Continued)

*Primary Examiner* — Anna Pagonakis
(74) *Attorney, Agent, or Firm* — Millen White Zelano and Branigan, PC; Csaba Henter (57) ABSTRACT

The present invention relates to a pharmaceutical composition which comprises progestogens, preferably drospirenone, estrogens, preferably ethinylestradiol and 5-methyl-(6S)-tetrahydrofolate, can be employed as oral contraceptive and moreover prevents disorders caused by folate deficiency in the consumers, in particular cardiovascular disorders and, after conception of the embryo, congenital malformations caused by folate deficiency such as, for example, neural tube defects, ventricular valve defects, urogenital defects, and cleft lip, jaw and palate, without masking the symptoms of vitamin $B_{12}$ deficiency, and at the same time even in the case of homozygous or heterozygous polymorphism of methylenetetrahydrofolate reductase facilitates unimpaired utilizability of the folate component 5-methyl-(6S)-tetrahydrofolate by the body and thus its biological activity for preventing the abovementioned congenital malformations caused by folate deficiency. In addition, a prolonged protective effect is maintained after discontinuation of the contraceptive.

29 Claims, 2 Drawing Sheets (51) Int. Cl.

| | | |
|---|---|---|
| *A61K 31/525* | (2006.01) | |
| *A61K 31/56* | (2006.01) | |
| *A61K 31/565* | (2006.01) | |
| *A61K 31/57* | (2006.01) | |
| *A61K 31/585* | (2006.01) | |
| *A61K 45/06* | (2006.01) | |
| *A61K 31/567* | (2006.01) | |

(52) U.S. Cl.
CPC ............ *A61K 31/56* (2013.01); *A61K 31/565* (2013.01); *A61K 31/567* (2013.01); *A61K 31/57* (2013.01); *A61K 31/585* (2013.01); *A61K 45/06* (2013.01)

(56) References Cited

U.S. PATENT DOCUMENTS

| | | | |
|---|---|---|---|
| 6,190,693 | B1 | 2/2001 | Kafrissen et al. |
| 6,326,392 | B1 | 12/2001 | Gast |
| 6,441,168 | B1 | 8/2002 | Muller |
| 6,787,531 | B1 | 9/2004 | Hilman |
| 6,921,754 | B2 | 7/2005 | Hahnlein et al. |
| 7,014,865 | B1 | 3/2006 | Buchholz |
| 2005/0164977 | A1 | 7/2005 | Coelingh Bennink |
| 2006/0034954 | A1 | 2/2006 | Bland et al. |
| 2016/0095860 | A1 | 4/2016 | Strothmann |

FOREIGN PATENT DOCUMENTS

| | | | |
|---|---|---|---|
| EP | 1888077 | B1 | 4/2009 |
| EP | 1044975 | B1 | 12/2009 |
| EP | 1632237 | B1 | 6/2017 |
| JP | 2001522798 | A | 11/2001 |
| JP | 2002527484 | A | 8/2002 |
| WO | 9727764 | | 8/1997 |
| WO | 9953910 | A2 | 10/1999 |
| WO | 2000066570 | A1 | 11/2000 |
| WO | 2001007024 | A2 | 2/2001 |
| WO | 2001015701 | A1 | 3/2001 |
| WO | 2001024772 | A1 | 4/2001 |
| WO | 03070255 | A1 | 8/2003 |
| WO | 2006120035 | A2 | 11/2006 |

OTHER PUBLICATIONS

Berge et al. "Pharmaceutical Salts." Journal of Pharmaceutical Sciences, 66(1), 1977:1-19.*
Tousey (Pharmaceutical Technology, Tableting & Granulation, 2002).*
Office Action dated Jun. 3, 2009, issued in connection with U.S. Appl. No. 11/938,688 (which has been identified as a related application).
McSherry, J., "Folate to prevent neural tube defects," Can Med Assoc J., Apr. 1, 1995, vol. 152, No. 7, pp. 1043.
Lamers, Y. et al: Supplementation with [6S]-5-methyltetrahydrofolate or folic acid equally reduces plasma total homocysteine concentrations in healthy women. (American Journal of Clinical Nutrition[2003], Volume Date 2004, 79 (3), 473-478).
Food and Drug Administration, Advisory Committee for Reproductive Health Drugs, Dec. 15, 2003, Questions to the Committee.
Farrow et al., Prolonged use of oral contraception before a planned pregnancy is associated with a decreased risk of delayed conception, Human Reproduction vol. 17, No. 10, pp. 2754-2761, 2002.
Nelen et al., Homocysteine and Folate Levels as Risk Factors for Recurrent Early Pregnancy Loss, Obstetrics & Gynecology vol. 95, No. 4, Apr. 2002, pp. 519-524.
The EFSA Journal (2004) 135, 1-20—Opinion of the Scientific Panel on Food Additives, Flavourings, Processing Aids and Materials in Contact with Food on a request from the Commission related to Calcium L-Methylfolate Question No. EFSA-Q-2004-007—Adopted on Oct. 28, 2004 by written procedure. (Author: Scientific Panel).
Venn, Bernard J. et al., "Comparison of the effect of low-dose supplementation with L-5-methyltetrahydrofolate or folic acid on plasma homocysteine: a randomized placebo-controlled study", Am J Clin Nutr 2003;77-658-62.
Venn, Bernard J. et al., "Increases in Blood Folate Indices Are Similar in Women of Childbearing Age Supplemented with [6S]-5-Methyltetrahydrofolate and Folic Acid", Human Nutrition and Metabolism Research Communication, The Journal of Nutrition—2002 American Society for Nutritional Sciences, pp. 3353-3355.
Pentieva, Kristina et al., "The Short-Term Bioavailabilities of [6S]-5-Methyltetrahydrofolate and Folic Acid Are Equivalent in Men"—The Journal of Nutrition—2004 American Society for Nutritional Sciences. Manuscript received Sep. 30, 2003. Initial review completed Oct. 21, 2003. Revision accepted Dec. 14, 2003.
Scott, John M., "Folate and vitamin B12"—Proceedings of the Nutrition Society (1999), 58, 441-448.
Scott, John M., et al., "The Methyl Folate Trap"—The Lancet, Aug. 15, 1981, pp. 337-340.
FDA Summary Minutes—Advisory Committee for Reproductive Health Drugs Meeting—Dec. 15, 2003—4 pages.
Prinz-Langenohl, Reinhild et al., "Beneficial role for folate in the prevention of colorectal and breast cancer", Eur J Nutr 40:98-105 (2001).
Czeizel, Andrew E., "Reduction of Urinary Tact and Cardiovascular Defects by Periconceptional Multivitamin Supplementation", American Journal of Medicine Genetics 62:179-183 (1996).
Encyclopedia of Pharmaceutical Technology—editors: James Swarbrick, James C. Bohlan—Apr. 20, 2015.
Submission dated Aug. 29, 2012 which was filed by the Applicant Bayer in respect of European patent application EP 2422774.
Remington's Pharmaceutical Sciences, Eighteen edition 1990, p. 594, Figure 31-9, Editor Gennaro et al.
Comparative Test Report—Reproduction of Example 1B of Bayer's EP 2,116,249 B1—Apr. 20, 2015.
Suarez de Ronderas, Maria del Pilar; Acta Med. Costarric, San José, vol. 45, No. 1, pp. 05-09, Mar. 2003 (English translation).
Faure et al: Process control and scale-up of pharmaceutical wet granulation processes: a review; Journal of Pharmaceutics and Biopharmaceutics; 52, issue 3, (2001) 269-277 (abstract).
Liebermann et al., Pharmaceutical Dosage Forms 1989; 195-200 (T.O.C).
Liebermann et al., Pharmaceutical Dosage Forms 1989; pp. 195-200.

* cited by examiner

Folate metabolism

THF: tetrahydrofolate
MTHFR: methylenetetrahydrofolate reductase
MS: methionine synthase
SAM: S-adenosylmethionine
SAH: S-adenosylhomocysteine

*FIG. 1*

FIG. 2

PHARMACEUTICAL COMPOSITION COMPRISING PROGESTOGENS AND/OR ESTROGENS AND 5-METHYL-(6S)-TETRAHYDROFOLATE

INCORPORATION BY REFERENCE

This application is a continuation-in-part of PCT patent application Serial No. PCT/EP2006/004858 filed May 15, 2006 which published as PCT Publication No. WO 2006/120035 on Nov. 16, 2006, which claims benefit of German patent application Serial Nos. 102005023301.5 filed May 13, 2005 and 102006016285.4 filed Apr. 3, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a pharmaceutical composition which comprises progestogens, estrogens and 5-methyl-(6S)-tetrahydrofolate, can be employed as oral contraceptive and moreover prevents disorders and malformations caused by folate deficiency, without at the same time masking the symptoms of vitamin $B_{12}$ deficiency.

BACKGROUND OF THE INVENTION

Drugs companies active in the area of fertility control are always making efforts to improve the available contraceptives. Included therein is not only increasing the contraceptive reliability by developing novel substances and an improved convenience of use. On the contrary, innovative approaches to combining contraception and disease prevention are also being pursued.

A number of diseases is regarded as being connected with a folate deficiency. Thus, administration of folates for example in the form of folic acid may minimize the risk of cardiovascular disorders and certain malignant disorders (such as, for example, carcinoma of the breast or colon).

Defects in the development of unborn children are particularly serious consequences of folate deficiency in women of childbearing age. Thus, women with low folate levels have an increased risk, compared with those having sufficiently high folate levels, of giving birth to children suffering from congenital malformations such as neural tube, ventricular valve and urogenital defects.

Neural tube defects are the commonest congenital malformations of the central nervous system. They arise through incomplete closure of the neural tube in about the third to fourth week of embryonic development. Neural tube defects include spina bifida (in some cases with meningocele or meningomyelocele), encephalocele and anencephalies which are characterized by partial or complete absence of areas of the brain. Children with anencephaly are virtually incapable of survival.

Spina bifida is distinguished by incomplete closure of vertebral arches. Its result, depending on the nature of the lesion, is life-long disability in the form of various sensory but also motor deficits—thus, for example, two thirds of children and adults are dependent on wheelchairs owing to muscular paralyses. Therapy entails covering the defect, fitting a shunt to drain the CSF and lengthy orthopedic and neurological rehabilitation. The costs of the medical treatment average 500 000 € per child.

It is assumed that there are about 250 000 neonates with neural tube defects around the world. The rate of neonatal impairments in Germany and the USA is about 1-2 per 1000 births. In Germany each year about 500 babies are born alive with neural tube defects, while a further 500 pregnancies have been terminated on the basis of prenatal ultrasonic diagnosis.

Sufficiently high folate levels at the time of conception and in the initial phase of pregnancy are crucial for avoiding neural tube defects. An erythrocyte folate level of at least 906 nmol/l is generally regarded as desirable for reducing the frequency of neural tube defects.

It is known that intake of folic acid at the right time around conception can reduce neural tube defects by 50-70%. The folic acid fortification of food products which is practiced in the USA has already markedly reduced the incidence of neural tube defects; in Canada and Chile in fact by more than 50%.

Both voluntary fortification of food products as, for example, in Germany, and intake of folic acid products does not, however, reach all women of childbearing age to a sufficient extent. Firstly, many women are unaware of the risk of neural tube defects and the possibility of minimizing a corresponding risk by intake of folic acid. Thus, in many countries, far fewer than 10% of them take folic acid products around the time of conception. Secondly, despite modern methods of contraception, which are increasingly easy to use, a large number of pregnancies—estimated at up to 50% in the USA (Inst. of Medicine 1998, NEJM 2004)— are unplanned, so that deliberate intake of folic acid products before conception is likewise precluded from the outset. In addition, for example in the USA, about 5-8% of users do not take oral contraceptives reliably.

The object on which the U.S. Pat. No. 6,190,693 (Kafrissen et al.) was based was therefore to prevent certain disorders which can be treated by folic acid in consumers of oral contraceptives. Kafrissen achieved this object by adding folic acid to an oral contraceptive. He disclosed a method for administering folic acid by use of a pharmaceutical composition which comprised both conventional substances with contraceptive activity and folic acid.

However, introduction of folic acid into oral contraceptives itself involves a serious health risk, because it may mask the early symptoms, which are still treatable, of a vitamin $B_{12}$ deficiency such as, for example, a megaloblastic anemia. This is because the hematological symptoms caused by vitamin $B_{12}$ deficiency can be treated so well by additional folate administration that a vitamin $B_{12}$ deficiency can be detected only with great difficulty, or not at all, and consequently therefore not diagnosed. The neuropsychiatric symptoms such as, for example, paresthesia and ataxia then remain untreated, however, and might deteriorate irreversibly.

The object on which the patent application WO 03/070255 (Coelingh Bennink) was based was therefore to avoid a health risk arising from the masking of the symptoms of a vitamin $B_{12}$ deficiency in consumers of folic acid-containing oral contraceptives. Coelingh Bennink achieves this object by adding vitamin $B_{12}$ to an oral contraceptive. He discloses a kit for oral hormonal contraception which comprises estrogens and/or progestogens, tetrahydrofolates and, obligatorily, vitamin $B_{12}$.

A further problem associated with the administration of folic acid and tetrahydrofolate products—which comprise no 5-methyl-(6S)-tetrahydrofolate—is the polymorphism of methylenetetrahydrofolate reductase (MTHFR C677T), which is heterozygous in about 55% of the Caucasian population and homozygous in about 10-15%. This polymorphism leads to a reduced activity of methylenetetrahydrofolate reductase, so that the women affected are unable to metabolize sufficiently the supplied folate and tetrahydrofolate into 5-methyl-(6S)-tetrahydrofolate, which is active in the body. This polymorphism is an acknowledged risk factor for disorders caused by folate deficiency, in particular for neural tube defects.

A further problem causing difficulties is that folic acid is a substance which does not naturally occur in foodstuffs. In order to be biologically active, it must first be converted metabolically by the enzyme dihydrofolate reductase into 7,8-dihydrofolate and (6S)-tetrahydrofolate. The metabolic capacity, in particular the first activation step, for conversion of the provitamin folic acid into its active reduced form is limited and moreover varies greatly from individual to individual. Since the enzyme dihydrofolate reductase does not play a role in the metabolism of metafolin, interactions between medicaments which inhibit dihydrofolate reductase, such as, for example, methotrexate and dihydrofolate reductase are not to be expected.

In order to provide an adequate supply of folate also to women suffering from methylenetetrahydrofolate reductase deficiency, EP 0898965 (Müller et al.) proposes the use of 5-methyl-(6S)-tetrahydrofolic acid or appropriate pharmaceutically acceptable salts as dietary supplement or as ingredient of medicaments. EP 1044975 A1 discloses inter alia stable crystalline salts of 5-methyl-(6S)-tetrahydrofolic acid and processes for their preparation.

It is known that a large proportion of pregnancies occurs shortly after discontinuing the contraceptive (Farrow et al., Human Reproduction Vol. 17, No., 10, pp. 2754-2761, 2002). If administration is irregular and unreliable, pregnancy may even occur during intake. It is likewise known that even after termination of additional folate administration a person can profit therefrom for a further 90 days or so (FDA Advisory Committee for Reproductive Health Drugs (ACRHD): The public health issues, including the safety and potential clinical benefit, associated with combining folic acid and an oral contraceptive into a single combination product. Dec. 15, 2003; Summary Minutes, Question 4). However, it is a precondition for this that folic acid has been taken in sufficiently large amount in addition to the normal diet in a sufficiently long preceding period. This so-called tissue depot effect can be seen through elevated folate levels in the erythrocytes.

It is further known that low folate/high homocysteine levels are associated with multiple spontaneous abortions (Merlen et al., Obstet. et Gynecol. 2000, 95: pp. 519-524).

Citation or identification of any document in this application is not an admission that such document is available as prior art to the present invention.

SUMMARY OF THE INVENTION

The present invention is based on the object of producing an oral contraceptive which, although able to prevent diseases caused by folate deficiency, at the same time is unable to mask the symptoms of vitamin $B_{12}$ deficiency. The invention is further based on the object of disclosing an administration regime which ensures that the consumer of the pharmaceutical composition of the invention is reliably protected also for a certain time after discontinuation from disorders or malformations caused by folate deficiency, in particular from neural tube defects. Both these also apply in the case of a homozygous or heterozygous polymorphism of methylenetetrahydrofolate reductase in the user, which adversely affects the utilizability of folic acid by the body and thus its biological activity to prevent neural tube defects.

The object is achieved according to the invention by a pharmaceutical composition comprising one or more progestogens and/or estrogens and 5-methyl-(6S)-tetrahydrofolate, and pharmaceutically acceptable excipients and carriers.

The invention is based on the realization, which is surprising in relation to WO 03/070255, that treatment and prevention of disorders caused by folate deficiency is possible even without masking symptoms of vitamin $B_{12}$ deficiency by administering solely 5-methyl-(6S)-tetrahydrofolate. Administration of vitamin $B_{12}$ is therefore no longer necessary in order to avoid the health risk described in WO 03/070255. Despite the administration of 5-methyl-(6S)-tetrahydrofolate, a physician is able to diagnose and, where appropriate, treat vitamin $B_{12}$ deficiency.

In the case of existing vitamin $B_{12}$ deficiency it is, of course, possible to administer vitamin $B_{12}$ in addition. The addition of further vitamins such as, for example, vitamin $B_6$ or vitamin $B_2$ is likewise optionally possible. The invention is further based on the realization, which is surprising in relation to WO 03/070255, that, unlike the administration of folates or other tetrahydrofolates, use solely of 5-methyl-(6S)-tetrahydrofolate in a contraceptive enables, even in a case of homozygous or heterozygous polymorphism of methylenetetrahydrofolate reductase, unlimited and adequate utilizability of the folate component by the body and thus its biological activity to prevent congenital malformations caused by folate deficiency.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
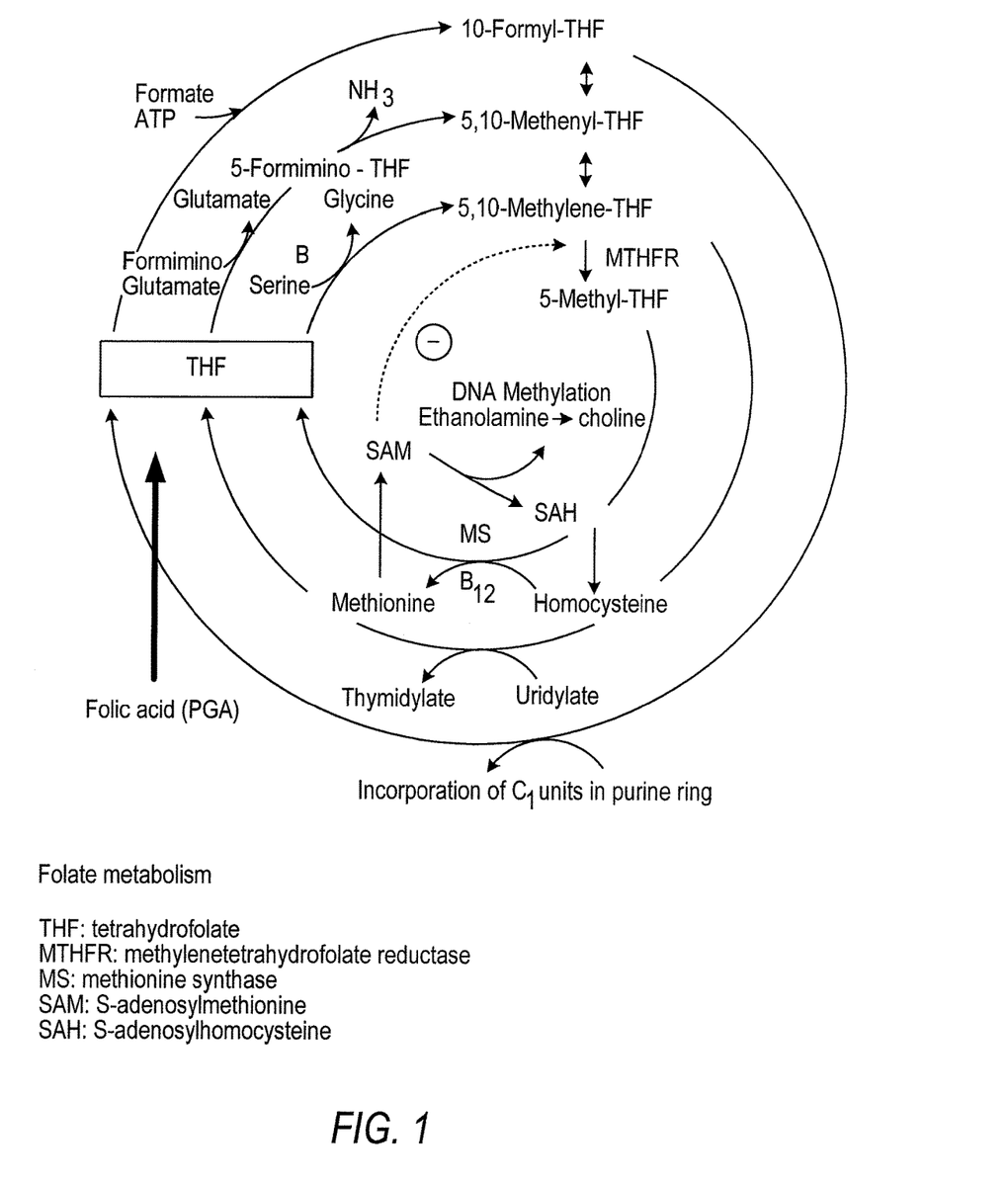
FIG. 1 depicts folate metabolism, wherein THF is tetrahydrofolate, MTHFR is methylenetetrahydrofolate reductase, MS is methionine synthase, SAM is S-adenosylmethionine and SAH is S-adenosylhomocysteine

5-Methyl-(6S)-tetrahydrofolate is synthesized metabolically (see FIG. 1) from 5,10-methylene-(6R)-tetrahydrofolate. This biochemical reaction is catalyzed by the enzyme methylenetetrahydrofolate reductase (MTHFR), of which various genetic mutations are known, some of which are manifested by restricted biological activity (MTHFR C677T polymorphism). 5-Methyl-(6S)-tetrahydrofolate is converted in a further step which is catalyzed by the enzyme methionine synthase (MS) into tetrahydrofolate. This entails transfer of the 5-methyl group of 5-methyl-(6S)-tetrahydrofolate to the amino acid homocysteine (Hcy) which is thus converted into the amino acid methionine (Met). This vitamin $B_{12}$-dependent reaction is also referred to as homocysteine methylation in homocysteine metabolism. 5-Methyl-(6S)-tetrahydrofolate occupies a special place in the group of reduced folates because 5-methyl-(6S)-tetrahydrofolate can be converted into tetrahydrofolate only by the homocysteine methylation reaction. Tetrahydrofolate is the actual carrier molecule for one-carbon units of various oxidation states. In metabolism, 5-methyl-(6S)-tetrahydrofolate can be synthesized only from 5,10-methylene-(6R)-tetrahydrofolate and can be further metabolized only by conversion into tetrahydrofolate. The first enzymatic reaction (MTHFR) is irreversible under physiological conditions, and the second enzymatic reaction (MS) is vitamin $B_{12}$-dependent, meaning that if there is a vitamin $B_{12}$ deficiency then 5-methyl-(6S)-tetrahydrofolate accumulates and cannot be metabolized further. This phenomenon is also known under the name methyl trap. Only 5-methyl-(6S)-tetrahydrofolate, but not any other oxidized and reduced folates such as folic acid, 7,8-dihydrofolate, (6S)-tetrahydrofolate, 5-formyl-(6S)-tetrahydrofolate, 10-formyl-(6R)-tetrahydrofolate, 5,10-methenyl-(6R)-tetrahydrofolate, 5,10-methylene-(6R)-tetrahydrofolate, 5-formimino-(6S)-tetrahydrofolate, displays this particular property. 5-Methyl-(6S)-tetrahydrofolate is the only naturally occurring folate which does not mask vitamin $B_{12}$ deficiency. This is of particular importance on use of 5-methyl-(6S)-tetrahydrofolate in combination with oral contraceptives and is an aspect of the present invention.

Progestogens which can be used in the pharmaceutical composition of the invention are the following substances: levonorgestrel, norgestimate, norethisterone, dyrogesterone, drospirenone, 3-beta-hydroxydesogestrel, 3-ketodesogestrel (=etonogestrel), 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol (=lynoestrenol), mecirogestone, medroxyprogesterone, megestrol, melengestrol, nomegestrol, norethindrone (=norethisterone), norethynodrel, norgestrel (including d-norgestrel and dl-norgestrel), norgestrienone, normethisterone, progesterone, quingestanol, (17alpha)-17-hydroxy-11-methylene-19-norpregna-4,15-dien-20-yn-3-one, tibolone, trimegestone, algestone acetophenide, nestorone, promegestone, 17-hydroxyprogesterone esters, 19-nor-17hydroxyprogesterone, 17alpha-ethynyltestosterone, 17alpha-ethynyl-19-nortestosterone, d-17beta-acetoxy-13beta-ethyl-17alpha-ethynylgon-4-en-3-one oxime or the compounds disclosed in WO 00/66570, especially tanaproget. Levonorgestrel, norgestimate, norethisterone, drospirenone, dydrogesterone are preferred. Drospirenone is particularly preferred.

Suitable estrogens are ethinylestradiol, mestranol, quinestranol, estradiol, estrone, estrane, estriol, estetrol and conjugated equine estrogens. In this connection ethinylestradiol, estradiol and mestranol are preferred, and ethinylestradiol is particularly preferred.

The amounts used according to the invention of the respective progestogens and/or estrogens correspond to the amounts normally known in contraceptives.

These amounts are normally for example for the progestogens mentioned below:

| | |
|---|---|
| Drospirenone | 0.5-5 mg |
| Levonorgestrel | 30-250 µg |
| Norgestimate | 180-250 µg |
| Norethisterone acetate | 0.5-1 mg |
| Cyproterone acetate | 1-2 mg |
| Desogestrel | 20-150 µg |
| Dienogest | 2-3 mg |
| Gestodene | 60-75 µg |
| Tibolone | 2.5 mg |

The preferred amount administered each day according to the present invention is for example 0.5 to 5 mg, particularly preferably 3 mg, of drospirenone.

The amount of estrogen used according to the invention is for instance for the estrogens mentioned below:

| | |
|---|---|
| Ethinylestradiol | 10-50 µg |
| Estradiol | 1-4 mg |
| Mestranol | 50 µg |

The preferred amount administered each day according to the invention is for example 10 to 50 µg, particularly preferably 10 to 30 µg, very particularly preferably 20 to 30 µg, of ethinylestradiol.

Reference to 5-methyl-(6S)-tetrahydrofolates in the form according to the invention means the free acid form and pharmaceutically acceptable salts and modifications of 5-methyl-(6S)-tetrahydrofolic acid (N-[4-[[(2-amino-1,4,5,6,7,8-hexahydro-4-oxo-5-methyl-(6S)-pteridinyl)methyl]amino]benzoyl]-L-glutamic acid).

Pharmaceutically acceptable salts are intended to be both pharmacologically and pharmaceutically acceptable. Such pharmacologically and pharmaceutically acceptable salts may be alkali metal or alkaline earth metal salts, preferably sodium, potassium, magnesium or calcium salts. The calcium salt is particularly preferred.

The amount used for example of the calcium salt, which is particularly preferred according to the invention, of 5-methyl-(6S)-tetrahydrofolic acid (metafolin) is between 0.1 and 10 mg, preferably 0.4 to 1 mg, particularly preferably 451 µg (equivalent to 400 µg of folic acid or 416 µg of 5-methyl-(6S)-tetrahydrofolic acid).

Crystalline modifications disclosed in EP 1044975 are preferably employed as modification of 5-methyl-(6S)-tetrahydrofolates.

It is optionally possible for vitamin $B_6$ or vitamin $B_2$ to be present. However, a corresponding addition is unnecessary to carry out the invention. Vitamin $B_6$ may be used in a dose between 1 mg and 5 mg, preferably between 1 mg and 3 mg per day on normally dosed use. Vitamin $B_2$ can be employed in a dose between 1 mg and 5 mg, preferably between 1 mg and 2 mg per day on normally dosed use, and between 2 and 5 mg per day on high-dosed use.

The progestogens and/or estrogens are the substances with contraceptive efficacy in this case. 5-Methyl-(6S)-tetrahydrofolate is added as vitamin in order to prevent disorders and malformations caused by folate deficiency without, however, at the same time masking the symptoms of vitamin $B_{12}$ deficiency which may be present. In addition, those women who, because of their reduced MTHFR enzymic activity (MTHFR C677T polymorphism), are capable of only restricted metabolism of folic acid, but also of reduced folates, also profit from 5-methyl-(6S)-tetrahydrofolate.

In the preferred variant of the present invention, the amount of drospirenone administered each day is 0.5 to 5 mg, preferably 3 mg, that of ethinylestradiol is 10 to 50 µg, preferably 10 to 30 µg, particularly preferably 20 to 30 µg. The calcium salt of 5-methyl-(6S)-tetrahydrofolic acid is present in an amount of from 0.1 to 10 mg, preferably 0.4 to 1 mg, particularly preferably 451 µg (equivalent to 400 µg of folic acid) in this preferred variant of the present invention.

The formulation of pharmaceutical products based on the novel pharmaceutical composition takes place in a manner known per se by processing the active ingredients with the carrier substances, fillers, substances influencing disintegration, binders, humectants, lubricants, absorbents, diluents, masking flavors, colorants and so on which are used in pharmaceutical technology, and converting into the desired administration forms, which also include slow-release forms.

In medicaments of the invention it is possible for the estrogen and the progestogen, and the 5-methyl-(6S)-tetrahydrofolate, to be present in joint dosage units. The estrogen with the progestogen on the one hand, and the 5-methyl-(6S)-tetrahydrofolate on the other hand, may, however, also be formulated in separate dose units.

Both vitamin $B_{12}$ and 5-methyl-(6S)-tetrahydrofolate are unstable in the presence of atmospheric oxygen and humidity. On attempting to formulate ethinylestradiol and vitamin $B_{12}$ together it was found that these two substances are incompatible with one another. Measurements of the incompatibilities between the intended formulation ingredients were carried out by a thermoanalytical method (DSC, differential scanning calorimetry). This allows incompatibilities to be recognized through low enthalpies of fusion and melting temperatures. These are caused for example by a reduced proportion of crystalline substance and the increase in impurities. In the determination, binary mixtures of excipients or active ingredients in each case with vitamin $B_{12}$ were investigated, and the compatibility was examined under the influence of various gases and temperatures. Vitamin $B_{12}$ showed a strong interaction with ethinylestradiol in the described investigations. The results of the incompatibility measurements may be found in Table 1.

TABLE 1

Summary of the compatibility investigation

| Substance | Compatibility | Type of compatibility | Comments |
|---|---|---|---|
| Drospirenone | + | mainly good | $O_2$-sensitive |
| Ethinylestradiol | --- | strong interaction | very $O_2$-sensitive |
| Ethinylestradiol β-cyclodextrin complex | + | mainly good below 60° C. | $O_2$-sensitive, moisture-sensitive |
| Lactose | + | mainly good below 60° C. | $O_2$-sensitive, moisture-sensitive |
| Corn starch | ++ | good below 60° C. | $O_2$-sensitive, moisture-sensitive |
| Modified corn starch | ++ | good below 60° C. | $O_2$-sensitive, moisture-sensitive |
| Polyvinylpyrrolidone | + | mainly good below 60° C. | $O_2$-sensitive, moisture-sensitive |

TABLE 1-continued

Summary of the compatibility investigation

| Substance | Compatibility | Type of compatibility | Comments |
|---|---|---|---|
| Magnesium stearate | ++/− | indifferent, good below 60° C. | $O_2$-sensitive, moisture-sensitive |
| Hydroxypropylmethyl-cellulose | ++ | good below 60° C. | $O_2$-sensitive, moisture-sensitive |
| Hydroxypropyl-cellulose | ++ | good below 60° C. | $O_2$-sensitive, moisture-sensitive |
| Maltodextrin | +/−− | indifferent, good below 60° C. | $O_2$-sensitive, moisture-sensitive |
| Polyethylene glycol 6000 | − | interaction with moisture | $O_2$-sensitive, moisture-sensitive |
| Coating mix | + | mainly good below 60° C. | $O_2$-sensitive, moisture-sensitive |

Key:
++ good compatibility expected below the stated temperature
+ compatibility below the stated temperature
++/− indifferent compatibility, possibly good compatibility below the stated temperature
+/−− indifferent compatibility, appears to be compatible below the stated temperature
−(−−−) (strong) interaction, incompatible Polyvinylpyrrolidone (PVP) is particularly suitable because of its wetting properties for hormone formulations (Moneghini et al., Int J Pharm 175, 1998, 177-183). However, formulation of 5-methyl-(6S)-tetrahydrofolate with PVP increases the rate of degradation of 5-methyl-(6S)-tetrahydrofolate (compare Table 2 and 3; process 3).

A further object on which this application was based and which is achieved by the present invention is therefore to make stable formulation of ethinylestradiol in the presence of 5-methyl-(6S)-tetrahydrofolate and optionally of vitamin $B_{12}$ possible.

It has been found that incompatibility between ethinylestradiol and vitamin $B_{12}$ can surprisingly be prevented by employing the ethinylestradiol in the formulation as ethinylestradiol-beta-cyclodextrin complex (ethinylestradiol as β-cyclodextrin clathrate; for preparation, compare WO 02/49675).

Corresponding formulations of the invention are described in Example 1 (compare composition A, B and D).

They comprise inter alia a mixture of corn starch and modified corn starch. Starch consists of amylose and amylopectin. Both are polysaccharides based on α-glucose units. However, it is also possible to use instead of corn starch in pharmaceutical formulations for example rice starch, potato starch or wheat starch.

The starch is employed swollen, suspended or dissolved as binding liquid or as solid. It may be unmodified or partly modified. The corn starch which is preferably used according to the invention has the empirical formula $(C_6H_{10}O_5)_n$ with n=300-1000. Its molecular weight is 50 000-160 000.

The starch used in pharmaceutical formulations serves only in part as pure filler. It is used otherwise as binder. 1-5%, preferably ∼1.8-3% of the tablet weight are to be added according to the invention as binder in the form of corn starch. Besides the corn starch, it is also possible to employ starch, a starch compound such as maltodextrin, or cellulose derivatives such as, for example, carboxymethyl-cellulose, ethylcellulose, hydroxypropylcellulose, hydroxypropylmethylcellulose or methylcellulose as binder. It is preferred according to the invention to use low-substituted cellulose derivatives. These have a viscosity of 1-20 mPas in a 2 percent aqueous solution. Derivatives with a viscosity of 2-20 mPas are preferred according to the invention, and those with a viscosity of 3-6 mPas are particularly preferred.

Part of the corn starch used in the formulation preferred according to the invention may be replaced by low-substituted hydroxypropylcellulose (HPC) in a concentration of 0.5-5% (w/w), preferably 1-3% (w/w), particularly preferably 2% (w/w). In the present case, the hydroxypropylcellulose has low substitution when no fewer than 5% and no more than 16% of its hydroxyl groups are esterified or etherified.

Table 2 shows the 5-methyl-(6S)-tetrahydrofolate content per tablet in % based on the specified content of 100% as a function of the binder used immediately after preparation. The 5-methyl-(6S)-tetrahydrofolate content shown was measured in the content uniformity test (CUT). The investigated formulation was prepared (process 2) by mixing the ingredients, granulating with the part of the corn starch used as binder, absorbing the 5-methyl-(6S)-tetrahydrofolate after completion of the granulation process, renewed mixing and tableting. By comparison therewith, polyvinylpyrrolidone was added as binder instead of corn starch to the formulation by process 3. The 5-methyl-(6S)-tetrahydrofolate content in the formulation prepared by process 3 is lower.

TABLE 2

Metafolin content as a function of the binder immediately after preparation

|  | Metafolin content absorption, PVP (process 3) | Metafolin content absorption, corn starch (process 2) |
|---|---|---|
| Average | 90.5% | 96.1% |

Table 3 shows the 5-methyl-(6S)-tetrahydrofolate content as a function of the binder used after storage at defined temperatures and humidity for one month. The tendency, evident from Table 2, for 5-methyl-(6S)-tetrahydrofolate formulated with PVP to be less stable is confirmed in particular on storage under conditions at 40° C. and 75% relative humidity (rH).

TABLE 3

Metafolin content as a function of the binder after storage

|  | 25° C./60% rH absorption PVP (process 3) | 25° C./60% rH absorption corn starch (process 2) | 40° C./75% rH absorption PVP (process 3) | 40° C./75% rH absorption corn starch (process 2) |
|---|---|---|---|---|
| Vials open | 89.5% | 92.1% | 37.7% | 67.7% |

An oral formulation is normally prepared by granulation, tableting and film-coating. However, 5-methyl-(6S)-tetrahydrofolate is, because of its sensitivity to oxygen and moisture, degraded even during the granulation. The further degradation of 5-methyl-(6S)-tetrahydrofolate during storage is, however, particularly noteworthy. In a formulation in which—as usual—all the components of the medicament, including 5-methyl-(6S)-tetrahydrofolate, are mixed first and only then granulated, the residue remaining after a storage time of one month at 40° C. and 75% relative humidity in closed vials was only just 60% (compare Table 5) of the originally employed 5-methyl-(6S)-tetrahydrofolate. The losses during the granulation process can be reduced by absorbing the 5-methyl-(6S)-tetrahydrofolate only after completion of the granulation process. Dry admixture during the preparation thus leads to stabilization of the 5-methyl-(6S)-tetrahydrofolate. However, in addition, this also surprisingly has the effect of further stabilization during storage. The 5-methyl-(6S)-tetrahydrofolate content in a formulation prepared by later absorption is above 90% with identical storage times under identical conditions (compare Table 5).

Table 4 shows the 5-methyl-(6S)-tetrahydrofolate content per tablet in % as a function of the preparation process used immediately after preparation. The difference between process 1 and process 2 derives from the time at which the 5-methyl-(6S)-tetrahydrofolate was added during the preparation of the investigated tablet. In process 1, the 5-methyl-(6S)-tetrahydrofolate was present in the mixture even during the granulation, whereas in process 2 it was absorbed only after the granulation. The 5-methyl-(6S)-tetrahydrofolate content in the formulation prepared by process 1 is distinctly lower.

TABLE 4

Metafolin content as a function of the preparation process immediately after preparation

|  | Metafolin content granulation (process 1) | Metafolin content absorption (process 2) |
|---|---|---|
| Average | 88.5% | 96.1% |
| Distribution coefficient | 6.1 | 2.5 |

Table 5 shows the 5-methyl-(6S)-tetrahydrofolate content as a function of the preparation process used after storage for one month at defined temperatures and humidity. The tendency, evident from Table 4, for 5-methyl-(6S)-tetrahydrofolate added before the granulation to be less stable is confirmed in particular on storage under conditions of 40° C. and 75% relative humidity (rH).

TABLE 5

Metafolin content as a function of the preparation process after storage

|  | 25° C./60% rH granulation (process 1) | 25° C./60% rH absorption (process 2) | 40° C./75% rH granulation (process 1) | 40° C./75% rH absorption (process 2) |
|---|---|---|---|---|
| Vials open | 63.2% | 92.1% | 43.4% | 67.7% |
| Vials closed | 74.5% | 92.5% | 58.9% | 90.1% |

Figure 2:
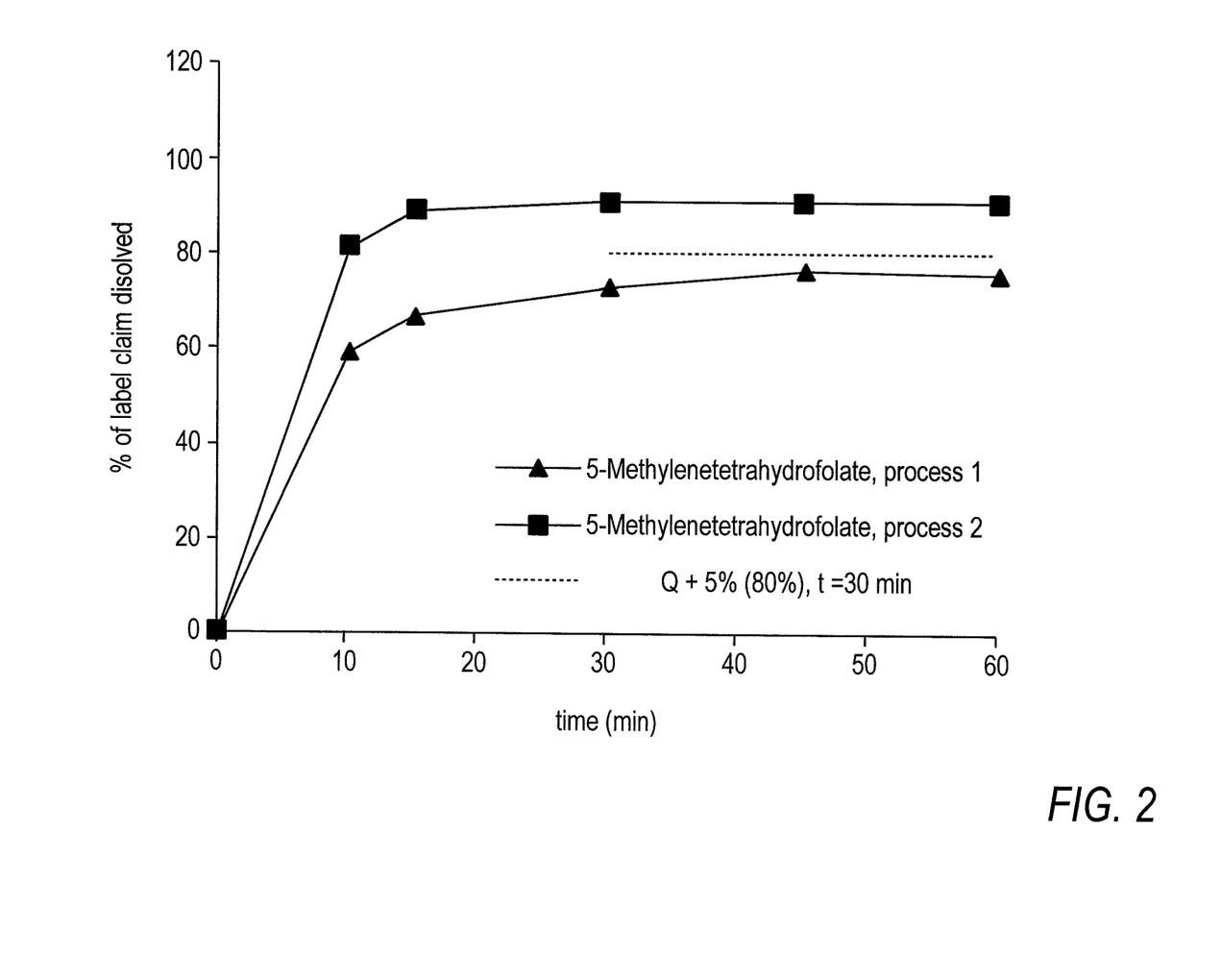
FIG. 2 depicts the results of the in vitro dissolution tests presented in Table 6.

It is known that release takes place more slowly with dry admixture than in the case of granulation. However, it was surprisingly found that dry admixture of the 5-methyl-(6S)-tetrahydrofolate does not delay release, but in fact accelerates it. For this purpose, the tablets were investigated in an in vitro dissolution test using a USP paddle apparatus at 50 rpm and 37° C. in a 0.03 percent aqueous ascorbic acid solution. Table 6 shows the results of the in vitro dissolution tests.

TABLE 6

| | Dissolution in % | |
|---|---|---|
| Time [min] | 5-Methyl-(6S)-tetrahydrofolate process 1 dissolution [%] | 5-Methyl-(6S)-tetrahydrofolate process 2 dissolution [%] |
| 0 | 0 | 0 |
| 10 | 59.2 | 81.4 |
| 15 | 66.8 | 89.3 |
| 30 | 73.1 | 91.3 |
| 45 | 76.7 | 91.1 |
| 60 | 75.8 | 91.2 |

Regular intake of the pharmaceutical composition of the invention with the particularly preferred dose of 451 µg of the calcium salt of 5-methyl-(6S)-tetrahydrofolic acid per day leads to an increase in the folate concentrations in the serum and erythrocytes until a steady state is reached. The corresponding erythrocyte folate invasion kinetics are described by half-life of from 6 to 10 weeks. On the basis of this half-life, about 97% of the steady-state erythrocyte folate level can be expected to be reached after about 5 half-lives (corresponding to about 30 to 50 weeks). If daily intake of the pharmaceutical composition of the invention is continued, the erythrocyte folate levels remain in the region of the steady-state concentrations. After discontinuation of the pharmaceutical composition of the invention, the erythrocyte folate levels slowly fall with a half-life likewise of about 6 to 10 weeks. The erythrocyte folate levels thus remain even without further continuation of intake of the pharmaceutical composition of the invention for several weeks in a range above the limit of 906 nmol/l which is generally regarded as sufficient to prevent neural tube defects. The product of the invention thus ensures a reduction in the risk of disorders caused by folate deficiency and congenital malformations caused by folate deficiency, even after termination of long-term intake of the medicament of the invention ("pill").

The use of 5-methyl-(6S)-tetrahydrofolate, one or more estrogens and/or progestogens, and optionally vitamin $B_6$ and/or vitamin $B_2$, and pharmaceutically acceptable excipients and carriers for producing a medicament for reducing the risk of disorders caused by folate deficiency and congenital malformations caused by folate deficiency for at least 8 weeks after termination of previous long-term and continual intake of this medicament is also according to the invention.

Likewise according to the invention is a kit comprising at least 20 daily dose units comprising the medicament of the invention and at least one daily dose unit comprising 5-methyl-(6S)-tetrahydrofolate, and optionally vitamin $B_{12}$, vitamin $B_6$ and/or vitamin $B_2$, where the number of all the dose units present in the kit is at least 28, and the dose units are disposed so that first the dose units comprising the medicament of the invention, and then the dose units comprising neither estrogen nor progestogen, are to be taken. It is also possible in the case of the first-mentioned at least 20 daily dose units comprising the medicament of the invention for the 5-methyl-(6S)-tetrahydrofolate to be formulated separately and to be disposed spatially as additional dose units such that joint intake of both dose units is evident from this disposition.

Further developments of the invention for different kits are reflected in kits of the below numbered paragraphs and claims.

It is also possible in particular, according to the below numbered paragraphs and claims, for the medicament of the invention to be administered in a so-called extended regime. By this is meant continuous administration of the medicament for more than 28 days, the extended cycle of use being completed by administration for 1 to 7 days of dose units exclusively comprising 5-methyl-(6S)-tetrahydrofolate or by intake of 1 to 7 placebos (dose units active agent) or 1 to 7 blank pill days (no administration of any dose unit).

The following examples serve to explain the subject matter of the invention in more detail without wishing to restrict it thereto.

Example 1

The composition of tablets (80 mg) of the invention can be found in Table 7.

TABLE 7

| | Composition of tablets of the invention | | | |
|---|---|---|---|---|
| | Amount Composition | | | |
| Ingredient | A | B | C | D |
| Drospirenone | 3 mg | 3 mg | — | 3 mg |
| Ethinylestradiol* | 0.03 mg | 0.02 mg | — | 0.03 mg |
| Metafolin | 0.451 mg | 0.451 mg | 0.451 mg | 0.451 mg |
| Vitamin B12 | — | — | — | 0.1 mg |
| Lactose monohydrate | to 80 mg | to 80 mg | to 80 mg | to 80 mg |
| Corn starch | 16.40 mg | 16.40 mg | 16.40 mg | 16.40 mg |
| Corn starch** | 2 mg*** | 2 mg*** | 2 mg*** | 2 mg*** |
| Modified corn starch | 9.60 mg | 9.60 mg | 9.60 mg | 9.60 mg |
| Magnesium stearate | 0.80 mg | 0.80 mg | 0.80 mg | 0.80 mg |

*optionally as ethinylestradiol-beta-cyclodextrin complex; the stated amount refers in this case to uncomplexed ethinylestradiol. If the ethinylestradiol-beta-cyclodextrin complex is used, about ten times the amount is to be employed. This is because the ethinylestradiol content in the β-cyclodextrin complex is about 9.5 to 12.5% (compare WO 02/49675).
the part of the corn starch identified by  can be replaced by an alternative binder such as, for example, 1.6 mg of low-substituted hydroxypropyl-cellulose.
*the amount of corn starch  employed as binder may also be for example 1.8 mg.

The oral formulation is produced by mixing the above-mentioned ingredients, granulating with the part of the corn starch used as binder, absorbing the calcium salt of 5-methyl-(6S)-tetrahydrofolic acid after completion of the granulation process, renewed mixing, tableting and film-coating.

Example 2

Blood is taken at 8-week intervals from 80 healthy young women of childbearing age, and the erythrocyte folate level is determined using a validated microbiological, immunological or instrumental (e.g. HPLC, LC-MS/MS) method or a suitable combination of these methods.

8 Weeks after the first blood sampling (screening phase), 451 µg of the calcium salt of 5-methyl-(6S)-tetrahydrofolic acid each day
is administered over a period of 40 weeks or, alternatively:
3 mg of drospirenone, 30 µg of ethinylestradiol and 451 µg of the calcium salt of 5-methyl-(6S)-tetrahydrofolic acid is administered simultaneously on each of the first 21 days of the respective cycle (tablet of composition A in Example 1). Administration of 451 µg of the calcium salt of 5-methyl-(6S)-tetrahydrofolic acid is continued for 7 days in a phase immediately subsequent thereto (composition C). 3 mg of drospirenone, 30 µg of ethinylestradiol and 451 µg of the calcium salt of 5-methyl-(6S)-tetrahydrofolic acid (composition A) are again administered for a further 21 days (second cycle), and only 451 µg of the calcium salt of 5-methyl-(6S)-tetrahydrofolic acid (composition C) are administered for a further 7 days, and so on (medication phase).

5-Methyl-(6S)-tetrahydrofolate is no longer administered after 48 weeks. Alternatively, drospirenone and ethinylestradiol can be administered further for a further 40 weeks or likewise be discontinued.

The last blood sample is taken after 88 weeks. The drop-out rate may be up to 50% because of the long-term nature of the study.

Example 3

Blood is taken at 8-week intervals from 80 healthy young women of childbearing age, and the erythrocyte folate level is determined using a validated microbiological, immunological or instrumental (e.g. HPLC, LC-MS/MS) method or a suitable combination of these methods.

Weeks after the first blood sampling, 3 mg of drospirenone, 20 µg of ethinylestradiol and 451 µg of the calcium salt of 5-methyl-(6S)-tetrahydrofolic acid (composition B) is administered simultaneously in each case in the first 24 days of the respective cycle for a period of 40 weeks. In a phase immediately subsequent thereto, administration of 451 µg of the calcium salt of 5-methyl-(6S)-tetrahydrofolic acid is continued for 7 days (composition C). For a further 21 days (second cycle), 3 mg of drospirenone and 20 µg of ethinylestradiol and 451 µg of the calcium salt of 5-methyl-(6S)-tetrahydrofolic acid (composition B) are again administered, and only 451 µg of the calcium salt of 5-methyl-(6S)-tetrahydrofolic acid (composition C) are administered for a further 7 days, and so on.

5-Methyl-(6S)-tetrahydrofolate is no longer administered after 48 weeks, while drospirenone and ethinylestradiol is administered further for a further 40 weeks or likewise discontinued.

The last blood sample is taken after 88 weeks. The drop-out rate may be up to 50% because of the long-term nature of the study.

The initial erythrocyte folate level in the subjects is about 500 to 700 nmol/l, depending on the eating habits, but is in every case below 906 nmol/l. This value rises on administration of the pharmaceutical composition of the invention in subsequent days, while the eating habits remain the same, and reaches a value of about 906 nmol/l after only 6 to 8 weeks—i.e. after the second cycle. After continuous administration for at least 30 weeks (corresponding to five times the lower limit of the half-life), while the eating habits remain the same, the erythrocyte folate level reaches about 1200 to 1600 nmol/l (steady state). After termination of the administration of 5-methyl-(6S)-tetrahydrofolate, the erythrocyte folate level falls continuously. Starting from an average steady state concentration of 1400 nmol/l and with the eating habits remaining the same, the erythrocyte folate level is expected to fall below 906 nmol/l, and thus the minimum concentration in erythrocytes generally sufficient to prevent neural tube defects, in the eleventh to thirteenth week after discontinuation of the pharmaceutical composition of the invention.

Example 4: Long-Term Folate Study 180 healthy young women of child-bearing age (half of whom receive a diet fortified with folic acid) have blood taken at intervals of 2 weeks, and the erythrocyte folate level is determined using a validated microbiological, immunological or instrumental (e.g. HPLC, LC-MS/MS) method or a suitable combination of these methods.

8 weeks after the first taking of blood, a first group of 90 women receives over a period of 24 weeks
administration of simultaneously 3 mg of drospirenone, 30 µg of ethinylestradiol and 451 µg of the calcium salt of 5-methyl-(6S)-tetrahydrofolic acid in each of the first 21 days of the respective cycle. In a phase directly subsequent thereto, administration of 451 µg of the calcium salt of 5-methyl-(6S)-tetrahydrofolic acid is continued for 7 days. For a further 21 days (second cycle), again 3 mg of drospirenone, 30 µg of ethinylestradiol and 451 µg of the calcium salt of 5-methyl-(6S)-tetrahydrofolic acid, and for a further 7 days only 451 µg of the calcium salt of 5-methyl-(6S)-tetrahydrofolic acid, are administered, and so on (medication phase).

A group of 90 women receive administration of 3 mg of drospirenone, 30 µg of ethinylestradiol and 400 µg of folic acid according to the same administration scheme as control group.

The last blood is taken in both cases after 24 weeks. This is followed by an observation period of 20 weeks in which the contraceptive product Yasmin® is administered for 20 weeks, i.e. in each of the first 21 days of the respective cycle, 3 mg of drospirenone and 30 µg of ethinylestradiol are administered simultaneously; directly subsequent thereto, no active substance is administered (placebos or no administration) for 7 days. The dropout rate may be up to 30%.

The initial erythrocyte folate level in the subjects is below 906 nmol/l. This value increases in subsequent days, if the eating habits remain the same, with administration of the pharmaceutical composition of the invention and, in most of the women, reaches a value of about 906 nmol/l after 6 to 8 weeks. After continuous administration for 24 weeks and with the eating habits remaining the same, an erythrocyte folate level is reached in both groups which shows equivalence between the two treatment groups (bioequivalence criterion 80-125%). After termination of administration of 5-methyl-(6S)-tetrahydrofolate, the erythrocyte folate level falls continuously. It is ascertained when the erythrocyte folate level falls below the acknowledged threshold of 906 nmol/l, which is generally regarded as sufficient to avoid neural tube defects.

Such an adequate erythrocyte folate level is still shown by most of the women in the first group 3 months after termination of intake.

The invention is further described by the following numbered paragraphs:

1. A medicament comprising:
   5-methyl-(6S)-tetrahydrofolate
   one or more estrogens, selected from the group of ethinylestradiol, mestranol, quinestranol, estradiol, estrone, estrane, estriol, estetrol and conjugated equine estrogens and/or progestogens,
   optionally vitamin $B_6$ and/or vitamin $B_2$,
   and pharmaceutically acceptable excipients/carriers
   in the absence of Vitamin $B_{12}$.
2. The medicament of paragraph 1, comprising at least one progestogen selected from the group of levonorgestrel, norgestimate, norethisterone, dydrogesterone, drospirenone, 3-beta-hydroxydesogestrel, 3-ketodesogestrel (=etonogestrel), 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol (=lynoestrenol), mecirogestone, medroxyprogesterone, megestrol, melengestrol, nomegestrol, norethindrone (=norethisterone), norethynodrel, norgestrel (including d-norgestrel and dl-norgestrel), norgestrienone, normethisterone, progesterone, quingestanol, (17alpha)-17-hydroxy-11-methylene-19-norpregna-4,15-dien-20-yn-3-one, tibolone, trimegestone, algestone-acetophenide, nestorone, promegestone, 17-hydroxyprogesterone esters, 19-nor-17hydroxyprogesterone, 17alpha-ethynyltestosterone, 17alpha-ethynyl-19-nortestosterone, d-17beta-acetoxy-13beta-ethyl-17alpha-ethynylgon-4-en-3-one oxime or the compounds disclosed in WO 00/66570, especially tanaproget.
3. The medicament of paragraph 1 comprising a crystalline calcium salt of 5-methyl-(6S)-tetrahydrofolic acid.
4. The medicament of paragraph 1, comprising 5-methyl-(6S)-tetrahydrofolate, drospirenone and ethinylestradiol.
5. The medicament of paragraph 4 comprising a daily dose of from 0.1 to 10 mg of 5-methyl-(6S)-tetrahydrofolate.
6. The medicament of paragraph 4 comprising a daily dose of from 0.4 to 1 mg of 5-methyl-(6S)-tetrahydrofolate.
7. The medicament of paragraph 4 comprising a daily dose of 451 μg of the calcium salt of 5-methyl-(6S)-tetrahydrofolic acid.
8. The medicament of paragraph 4 comprising a daily dose of from 0.5 to 5 mg of drospirenone.
9. The medicament of paragraph 4 comprising a daily dose of 3 mg of drospirenone.
10. The medicament of paragraph 4 comprising a daily dose of from 10 to 50 μg of ethinylestradiol.
11. The medicament of paragraph 4 comprising a daily dose of from 10 to 30 μg of ethinylestradiol.
12. The medicament of paragraph 4 comprising a daily dose of 20 μg of ethinylestradiol.
13. The medicament of paragraph 4 comprising a daily dose of 30 μg of ethinylestradiol.
14. The medicament of paragraph 4 comprising
    a daily dose of 451 μg of the calcium salt of 5-methyl-(6S)-tetrahydrofolic acid,
    a daily dose of 3 mg of drospirenone and
    a daily dose of 20 μg of ethinylestradiol.
15. The medicament of paragraph 4 comprising
    a daily dose of 451 μg of the calcium salt of 5-methyl-(6S)-tetrahydrofolic acid,
    a daily dose of 3 mg of drospirenone and
    a daily dose of 30 μg of ethinylestradiol.
16. A kit comprising
    at least 20 daily dose units comprising a medicament of any of the preceding paragraphs and
    at least one daily dose unit comprising 5-methyl-(6S)-tetrahydrofolate, and optionally vitamin $B_6$ and/or vitamin $B_2$,
    where the number of all the dose units present in the kit is at least 28 and
    the dose units are disposed so that first the dose units comprising the medicament of any of the preceding paragraphs, and subsequently the dose units comprising only 5-methyl-(6S)-tetrahydrofolate, are to be taken.
17. The kit of paragraph 16 comprising
    20-30 daily dose units comprising a medicament of any of paragraphs 1 to 15 and
    1-10 daily dose units comprising 5-methyl-(6S)-tetrahydrofolate.
18. The kit of paragraph 16 comprising
    21-26 daily dose units comprising a medicament of any of paragraphs 1 to 15 and
    2-7 daily dose units comprising 5-methyl-(6S)-tetrahydrofolate
    where the number of all the dose units present in the kit is 28.
19. The kit of paragraph 16 comprising
    21 daily dose units comprising a medicament of any of paragraphs 1 to 15 and
    7 daily dose units comprising 5-methyl-(6S)-tetrahydrofolate.
20. The kit of paragraph 16 comprising
    24 daily dose units comprising a medicament of any of paragraphs 1 to 15 and
    4 daily dose units comprising 5-methyl-(6S)-tetrahydrofolate.
21. The kit of paragraph 16 comprising 451 μg of the calcium salt of 5-methyl-(6S)-tetrahydrofolic acid in each daily dose unit.
22. The use of
    5-methyl-(6S)-tetrahydrofolate
    one or more estrogens, selected from the group of ethinylestradiol, mestranol, quinestranol, estradiol, estrone, estrane, estriol, estetrol or conjugated equine estrogen and/or progestogens,
    optionally vitamin $B_6$ and/or vitamin $B_2$,
    and pharmaceutically acceptable excipients/carriers
    in the absence of Vitamin $B_{12}$,
    for producing a medicament for reducing the risk of disorders caused by folate deficiency and congenital malformations caused by folate deficiency for at least 6-10 weeks after termination of previous long-term and continual intake of this medicament.
23. The use of paragraph 22, characterized in that the preceding long-term regular intake amounts to at least 30 weeks.

24. The use of either of paragraphs 22 or 23, where the progestogen is selected from the group of levonorgestrel, norgestimate, norethisterone, dydrogesterone, drospirenone, 3-beta-hydroxydesogestrel, 3-ketodesogestrel (=etonogestrel), 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol (=lynoestrenol), mecirogestone, medroxyprogesterone, megestrol, melengestrol, nomegestrol, norethindrone (=norethisterone), norethynodrel, norgestrel (including d-norgestrel and dl-norgestrel), norgestrienone, normethisterone, progesterone, quingestanol, (17alpha)-17-hydroxy-11-methylene-19-norpregna-4,15-dien-20-yn-3-one, tibolone, trimegestone, algestone acetophenide, nestorone, promegestone, 17-hydroxyprogesterone esters, 19-nor-17hydroxyprogesterone, 17alpha-ethynyltestosterone, 17alpha-ethynyl-19-nortestosterone, d-17beta-acetoxy-13beta-ethyl-17alpha-ethynylgon-4-en-3-one oxime or the compounds disclosed in WO 00/66570, especially tanaproget.

25. The use of paragraph 23 or 24 for reducing the risk of neural tube defects.

26. The use of paragraph 23 or 24 for reducing the risk of cardiac defects, in particular ventricular valve defects.

27. The use of paragraph 23 or 24 for reducing the risk of malformations of the urinary tract (urogenital defects).

28. The use of paragraph 23 or 24 for reducing the risk of cleft lip, jaw and palate.

29. The use of paragraph 23 or 24 for reducing the risk of spontaneous abortions.

30. The use of paragraph 23 or 24 for reducing the risk of malignant disorders, in particular carcinoma of the breast or colon.

31. The use of paragraph 23 or 24 for reducing the risk of cardiovascular disorders.

32. The use of 5-methyl-(6S)-tetrahydrofolate, drospirenone and ethinylestradiol of paragraph 25 to 31.

33. The use of 451 µg of the calcium salt of 5-methyl-(6S)-tetrahydrofolic acid, 3 mg of drospirenone and 20 µg of ethinylestradiol of paragraph 25 to 31.

34. The use of 451 µg of the calcium salt of 5-methyl-(6S)-tetrahydrofolic acid, 3 mg of drospirenone and 30 µg of ethinylestradiol of paragraph 25 to 31.

35. The use of paragraph 22 or 23, characterized in that the preceding intake of at least 5-methyl-(6S)-tetrahydrofolate takes place in a slow-release form.

36. The kit of paragraph 16, comprising
    21 daily dose units comprising a medicament of paragraph 14 and
    7 daily dose units comprising 5-methyl-(6S)-tetrahydrofolate.

37. The kit of paragraph 16, comprising
    24 daily dose units comprising a medicament of paragraph 14 and
    4 daily dose units comprising 5-methyl-(6S)-tetrahydrofolate.

38. The kit of paragraph 16, comprising
    21 daily dose units comprising a medicament of paragraph 15 and
    7 daily dose units comprising 5-methyl-(6S)-tetrahydrofolate.

39. A method for formulating the medicament of any of paragraphs 1 to 15, characterized in that the 5-methyl-(6S)-tetrahydrofolate is absorbed only after the granulation.

40. The method of paragraph 39, characterized in that low-substituted hydroxypropylcellulose is used as binder.

41. The kit of paragraph 16, comprising more than 28 daily dose units, where at least 28 daily dose units comprise a medicament of any of paragraphs 1 to 15, and where at least one daily dose unit comprises 5-methyl-(6S)-tetrahydrofolate, and where the dose units are disposed so that firstly the dose units comprising the medicament of any of paragraphs 1 to 15, and subsequently the dose units comprising only 5-methyl-(6S)-tetrahydrofolate, are to be taken.

42. The kit of paragraph 41, in which the number of dose units comprising a medicament of any paragraphs 1 to 15 is 28 plus 21, 22, 23, 24, 25, 26 or 27 or an integral multiple of 28 plus 21, 22, 23, 24, 25, 26 or 27, and where the number of daily dose units which comprise only 5-methyl-(6S)-tetrahydrofolate is 7, 6, 5, 4, 3, 2 or 1.

43. The kit of paragraph 42, in which the multiple is 2, 3, 4, 5, 6, 7, 8, 9, 10, 11 or 12.

44. A kit comprising more than 28 daily dose units, where at least 28 daily dose units comprise a medicament of any of paragraphs 1 to 15, where at least one daily dose unit is a placebo or a blank pill day, and where the dose units are disposed so that first the dose units comprising the medicament of any of paragraphs 1 to 15 are to be taken.

45. The kit of paragraph 44, in which the number of dose units comprising of any of paragraphs 1 to 15 is 28 plus 21, 22, 23, 24, 25, 26 or 27 or an integral multiple of 28 plus 21, 22, 23, 24, 25, 26 or 27, and where the number of placebos or blank pill days is 7, 6, 5, 4, 3, 2 or 1.

46. The kit of paragraph 45, in which the multiple is 2, 3, 4, 5, 6, 7, 8, 9, 10, 11 or 12.

47. The kit of any of paragraphs 41 to 46, in which the dose units comprising medicament comprise a medicament of paragraph 14.

48. The kit of any of paragraphs 41 to 46, in which the dose units comprising medicament comprise a medicament of paragraph 15.

What is claimed is:

1. A process for preparing a medicament comprising 5-methyl-(6S)-tetrahydrofolate, one or more estrogens and/or progestogens, optionally vitamin $B_6$ and/or vitamin $B_2$, and a pharmaceutically acceptable carrier, the process comprising
    granulating the one or more estrogens and/or progestogens, optionally vitamin Bo and/or vitamin $B_2$, and the pharmaceutically acceptable carrier, such that granules are formed,
    thereafter absorbing the 5-methyl-(6S)-tetrahydrofolate onto and/or into said granules, wherein the absorption of the 5-methyl-(6S)-tetrahydrofolate onto and/or into said granules is performed by dry admixture.

2. The process of claim 1 wherein said medicament comprises dienogest and no estrogen.

3. The process of claim 1 wherein said medicament comprises estrogen and progestogen.

4. The process of claim 1 wherein said medicament comprises progestogen and no estrogen.

5. The process of claim 1 wherein said medicament comprises a crystalline calcium salt of 5-methyl-(6S)-tetrahydrofolic acid.

6. The process of claim 1 wherein said medicament comprises a daily dose of 451 µg of the calcium salt of 5-methyl-(6S)-tetrahydrofolic acid.

7. The process of claim 1 wherein said medicament comprises an amount of dienogest as a daily dose of 2-3 mg.

8. The process of claim 6 wherein said medicament comprises a daily dose of 451 µg of the calcium salt of 5-methyl-(6S)-tetrahydrofolic acid.

9. The process of claim 1 wherein said medicament comprises dienogest and a pharmaceutically acceptable estradiol salt.

10. The process of claim 1 wherein said medicament comprises estrogen and no progestogen.

11. The process of claim 1 wherein the medicament is free of folic acid.

12. The process of claim 10 wherein the medicament is free of folic acid.

13. The process of claim 1 wherein the granulation of the one or more estrogens and/or progestogens, optionally vitamin $B_6$ and/or vitamin $B_2$, and the pharmaceutically acceptable carrier is performed in the presence of a binder, and wherein the formed granules further contain said binder.

14. The process of claim 13 wherein the binder is starch.

15. A process for preparing a medicament comprising 5-methyl-(6S)-tetrahydrofolate, at least one estrogen which is ethinylestradiol, mestranol, quinestranol, estradiol, estrone, estrane, estriol, estetrol or conjugated equine estrogens, and/or at least one progestogen, and a pharmaceutically acceptable carrier, the process comprising granulating the at least one estrogen which is ethinylestradiol, mestranol, quinestranol, estradiol, estrone, estrane, estriol, estetrol or conjugated equine estrogens, and/or at least one progestogen, and the pharmaceutically acceptable carrier, such that granules are formed, thereafter absorbing the 5-methyl-(6S)-tetrahydrofolate onto and/or into said granules, wherein the absorption of the 5-methyl-(6S)-tetrahydrofolate onto and/or into said granules is performed by dry admixture.

16. The process of claim 15 wherein the granulation of the at least one estrogen which is ethinylestradiol, mestranol, quinestranol, estradiol, estrone, estrane, estriol, estetrol or conjugated equine estrogens, and/or at least one progestogen, and the pharmaceutically acceptable carrier is performed in the presence of a binder, and wherein the formed granules further contain said binder.

17. The process of claim 16 wherein the binder is starch.

18. The process of claim 15, wherein said at least one progestogen is levonorgestrel, norgestimate, norethisterone, dydrogesterone, drospirenone, 3-beta-hydroxydesogestrel, 3-ketodesogestrel (=etonogestrel), 17-deacetylnorgestimate, 19-norprogesterone, acetoxypregnenolone, allylestrenol, amgestone, chlormadinone, cyproterone, demegestone, desogestrel, dienogest, dihydrogesterone, dimethisterone, ethisterone, ethynodiol diacetate, fluorogestone acetate, gastrinone, gestodene, gestrinone, hydroxymethylprogesterone, hydroxyprogesterone, lynestrenol (=lynoestrenol), mecirogestone, medroxyprogesterone, megestrol, melengestrol, nomegestrol, norethindrone (=norethisterone), norethynodrel, norgestrel (including d-norgestrel and dl-norgestrel), norgestrienone, normethisterone, progesterone, quingestanol, (17alpha)-17-hydroxy-11-methylene-19-norpregna-4, 15-dien-20-yn-3-one, tibolone, trimegestone, algestone-acetophenide, nestorone, promegestone, a 17-hydroxyprogesterone esters, 19-nor-17hydroxyprogesterone, 17alpha-ethynyltestosterone, 17alpha-ethynyl-19-nortestosterone, d-17beta-acetoxy-13beta-ethyl-17alpha-ethynylgon-4-en-3-one oxime or tanaproget.

19. The process of claim 15 wherein said medicament comprises a crystalline calcium salt of 5-methyl-(6S)-tetrahydrofolic acid.

20. The process of claim 18 wherein said medicament comprises a crystalline calcium salt of 5-methyl-(6S)-tetrahydrofolic acid.

21. The process of claim 18 wherein said medicament comprises a crystalline calcium salt of 5-methyl-(6S)-tetrahydrofolic acid, drospirenone and ethinylestradiol.

22. The process of claim 18 wherein said medicament comprises d- or dl-norgestrel.

23. The process of claim 21 wherein said medicament comprises a daily dose of from 0.1 to 10 mg of said calcium salt, a daily dose of from 0.5 to 5 mg of drospirenone and a daily dose of from 10 to 50 µg of ethinylestradiol.

24. The process of claim 21 wherein said medicament comprises a daily dose of from 0.1 to 10 mg of said calcium salt, a daily dose of from 0.5 to 5 mg of drospirenone and a daily dose of from 10 to 30 µg of ethinylestradiol.

25. The process of claim 21 wherein said medicament comprises a daily dose of from 0.4 to 1 mg of said calcium salt, a daily dose of 3 mg of drospirenone and a daily dose of from 10 to 30 µg of ethinylestradiol.

26. The process of claim 21 wherein said medicament comprises a daily dose of from 0.1 to 10 mg of said calcium salt, a daily dose of 3 mg of drospirenone and a daily dose of from 10 to 30 µg of ethinylestradiol.

27. The process of claim 21 wherein said medicament comprises a daily dose of from 0.4 to 1 mg of said calcium salt, a daily dose of from 0.5 to 5 mg of drospirenone and a daily dose of from 10 to 30 µg of ethinylestradiol.

28. The process of claim 21 wherein said medicament comprises a daily dose of 451 µg of the calcium salt of 5-methyl-(6S)-tetrahydrofolic acid, a daily dose of 3 mg of drospirenone and a daily dose of 20 µg of ethinylestradiol.

29. The process of claim 21 wherein said medicament comprises a daily dose of 451 µg of the calcium salt of 5-methyl-(6S)-tetrahydrofolic acid, a daily dose of 3 mg of drospirenone and a daily dose of 30 µg of ethinylestradiol.

* * * * *